United States Patent
Minami et al.

(10) Patent No.: US 8,069,859 B2
(45) Date of Patent: Dec. 6, 2011

(54) WRAPPING PAPER INSPECTION APPARATUS AND TOBACCO WRAPPING MACHINE

(75) Inventors: Keisuke Minami, Tokyo (JP); Tsuyoshi Futamura, Tokyo (JP)

(73) Assignee: Japan Tobacco Inc., Tokyo (JP)

(*) Notice: Subject to any disclaimer, the term of this patent is extended or adjusted under 35 U.S.C. 154(b) by 521 days.

(21) Appl. No.: 11/152,142

(22) Filed: Jun. 15, 2005

(65) Prior Publication Data
US 2005/0229941 A1    Oct. 20, 2005

Related U.S. Application Data

(63) Continuation of application No. PCT/JP03/016350, filed on Dec. 19, 2003.

(30) Foreign Application Priority Data

Dec. 20, 2002  (JP) ................................ 2002-370227

(51) Int. Cl.
 *A24C 5/38* (2006.01)
 *A24C 5/60* (2006.01)
(52) U.S. Cl. ........ 131/284; 162/198; 162/192; 356/429; 356/430; 356/431; 131/905; 131/907; 348/88
(58) Field of Classification Search .................. 131/284
 See application file for complete search history.

(56) References Cited

U.S. PATENT DOCUMENTS

| | | | | |
|---|---|---|---|---|
| 4,344,382 A | * | 8/1982 | Hausler et al. | 118/674 |
| 4,345,150 A | * | 8/1982 | Tamura et al. | 250/339.1 |
| 4,709,157 A | * | 11/1987 | Shimizu et al. | 250/559.46 |
| 5,426,509 A | * | 6/1995 | Peplinski | 356/430 |
| 6,020,969 A | | 2/2000 | Struckhoff et al. | |

FOREIGN PATENT DOCUMENTS

| | | |
|---|---|---|
| EP | 0898165 A2 | 2/1999 |
| JP | 60-114183 A | 6/1985 |
| JP | 6-10299 A | 1/1994 |
| JP | 2001-509366 A | 7/2001 |
| WO | 99/02976 A1 | 1/1999 |
| WO | WO 02/091865 A1 | 11/2002 |

* cited by examiner

*Primary Examiner* — Richard Crispino
*Assistant Examiner* — Phu Nguyen
(74) *Attorney, Agent, or Firm* — Birch, Stewart, Kolasch & Birch, LLP

(57) ABSTRACT

A wrapping paper inspection apparatus includes a nozzle arranged in a wrapping-paper discharge path, in which wrapping paper is wound and continuously discharged, for wetting one side of the wrapping paper with a liquid; an image pickup section for irradiating light to the wrapping paper wetted with the liquid by the nozzle, detecting light transmitted through or reflected from the wrapping paper, and generating an image signal; and a wrapping paper inspection section for determining defects in wrapping paper portions applied or affixed with a low flame spread material, from the image signal generated by the image pickup section, to thereby inspect such defects easily and reliably. This inspection apparatus can be mounted to a tobacco wrapping machine.

11 Claims, 5 Drawing Sheets

WRAPPING PAPER INSPECTION APPARATUS AND TOBACCO WRAPPING MACHINE

This application is a Continuation of copending PCT International Application No. PCT/JP2003/016350 filed on Dec. 19, 2003, which designated the United States, and on which priority is claimed under 35 U.S.C. §120. This application also claims priority under 35 U.S.C. §119(a) on Patent Application No(s). 2002-370227 filed in Japan on Dec. 20, 2002. The entire contents of each of the above documents is hereby incorporated by reference.

TECHNICAL FIELD

This invention relates to an apparatus for inspecting the quality of wrapping paper used for making cigarettes, and more particularly, to a wrapping paper inspection apparatus for inspecting the quality of those portions of wrapping paper to which a low flame spread material is applied or affixed, and a tobacco wrapping machine provided with this type of inspection apparatus.

BACKGROUND ART

Cigarettes are generally manufactured by wrapping tobacco shreds with wrapping paper to form a tobacco rod and cutting the tobacco rod to a predetermined length. The wrapping paper is an elongated one—about 27 mm in width, and is provided in the rolled-up form, i.e., in the form of a roll.

Incidentally, a smoker sometimes drops a cigarette on a floor, a carpet or the like while smoking. In such cases, the cigarette should preferably stop burning naturally. To this end, attempts have been made to form wrapping paper with low flame spread portions. For instance, wrapping paper is increased in thickness by, for example, affixing pieces of paper containing a low flame spread material to one side of wrapping paper in approximately equally spaced stripes, or a diluted solution of a low flame spread material is coated on (applied to) wrapping paper in approximately equally spaced stripes, or other processing is done. Another attempt to inspect the quality of low flame spread portions of wrapping paper has also been made.

For example, a wrapping paper inspection apparatus described in Japanese national patent publication (Tokuhyo) no. 2001-509366 is designed to inspect wrapping paper consisting of base cigarette paper to which pulp layers of cellulose (microcrystalline cellulose, amylopectin or the like), which is a low flame spread material, are affixed in approximately equally spaced stripes. Specifically, this inspection apparatus is designed to irradiate light from a light source such as an infrared emitting diode to the wrapping paper while unwinding it from a roll, detect variation in the amount of light reflected from the wrapping paper by an optical sensor, and optically determine the quality of affixation of the pulp layers of low flame spread material to the wrapping paper.

In other words, this wrapping paper inspection apparatus uses a difference in light reflectance between the base cigarette paper of the wrapping paper and the low flame spread material affixed thereto, and is designed that spot light is irradiated onto one side of the wrapping paper to which the low flame spread material is affixed, and light that is reflected therefrom and transmitted through a detector lens, a filter, and a polarizer, is detected by a detector.

As mentioned above, there is wrapping paper having a low flame spread property imparted by increasing the thickness by affixing a material to base cigarette paper, the material having the same property as the base cigarette paper. In this type of wrapping paper where the base cigarette paper and the low flame spread portion are the same in material and there is no difference in light reflectance therebetween, it is impossible to detect defects in the low flame spread portion by using a difference in light reflectance between the base cigarette paper and the low flame spread material.

Wrapping paper applied with sodium alginate, which is a low flame spread material, also has a problem that it is difficult to reliably detect defects in the coating of the low flame spread material, since there is no noticeable difference in light reflectance between base cigarette paper and regions coated with sodium alginate.

DISCLOSURE OF THE INVENTION

This invention has been made considering the above circumstances, and has an object to provide a wrapping paper inspection apparatus capable of easily and reliably inspecting defects in those portions of wrapping paper used for making cigarettes to which a low flame spread material is applied or affixed, and a tobacco wrapping machine provided with a wrapping paper inspection apparatus of this type.

In order to achieve the object, according to this invention, there is provided a wrapping paper inspection apparatus for inspecting wrapping paper with a low flame spread material arranged in stripes on one side thereof, which comprises a nozzle arranged in a wrapping-paper discharge path, in which the wrapping paper is unwound and continuously discharged, for wetting the one side of the wrapping paper with a liquid; an image pickup section for irradiating light to the wrapping paper wetted with the liquid by the nozzle, picking up light transmitted through the wrapping paper or light reflected from the one side of the wrapping paper, and generating an image signal; and a wrapping paper inspection section for determining defects in the low flame spread material on the wrapping paper from the image signal generated by the image pickup section.

In the wrapping paper inspection apparatus of this invention, when the side of wrapping paper on which a low flame spread material is arranged in stripes is wetted with a liquid, the degree of infiltration of the liquid into the wrapping paper differs between the low flame spread material portions and the other portions of the wrapping paper. This produces a difference in light transmittance or reflectance therebetween, making it possible to reliably inspect defects in the low flame spread material portions of the wrapping paper (for example, defects in the application or affixation of the low flame spread material to the wrapping paper).

In this invention, the wrapping paper inspection section can include an image processing section for converting the image signal generated by the image pickup section into a luminance signal; a determination section for determining defects in the low flame spread material on the wrapping paper by comparing the luminance signal obtained by conversion in the image processing section with a predetermined luminance value; and a recording section for recording the defects in the low flame spread material on the wrapping paper determined by the determination section.

It is desirable that the liquid sprayed through the nozzle to wet the wrapping paper should be a liquid infiltrative to the wrapping paper. For example, water or a volatile liquid is used.

The invention also provides a tobacco wrapping machine for continuously wrapping tobacco shreds with wrapping paper with a low flame spread material arranged in stripes on one side thereof to form a tobacco rod, then cutting the tobacco rod to a predetermined length, and successively supplying tobacco rods of the predetermined length to a next process. This tobacco wrapping machine comprises a nozzle arranged in a wrapping-paper feeding path, in which the wrapping paper is unwound and continuously fed, for wetting the one side of the wrapping paper with a liquid; an image pickup section for irradiating light to the wrapping paper wetted with the liquid by the nozzle, picking up light transmitted through the wrapping paper or light reflected from the one side of the wrapping paper, and generating an image signal; and a wrapping paper inspection section for determining whether there are defects in the low flame spread material on the wrapping paper from the image signal generated by the image pickup section, and recording a result of determination.

Thus, it is possible to reliably inspect defects in those portions of the wrapping paper to which the low flame spread material is arranged, using a difference in light transmittance or reflectance between the low flame spread material portions of the wrapping paper and the other portions thereof. Further, it is possible to make cigarettes, with the wrapping paper unwound at a high speed, while continuously inspecting whether there are defects in the low flame spread material portions of the wrapping paper by means of a wrapping paper inspection apparatus including a nozzle arranged in the wrapping-paper feeding path and the like.

In this invention, it is desirable that the liquid sprayed through the nozzle to wet the wrapping paper should be a liquid infiltrative to the wrapping paper. For example, water or a volatile liquid is used. In this case, the liquid quickly diffuses into the wrapping paper after the inspection, which makes it possible to detect defects in the low flame spread material portions of the wrapping paper reliably, at a high speed, and without obstructing cigarette making.

BEST MODE OF CARRYING OUT THE INVENTION

Figure 1:
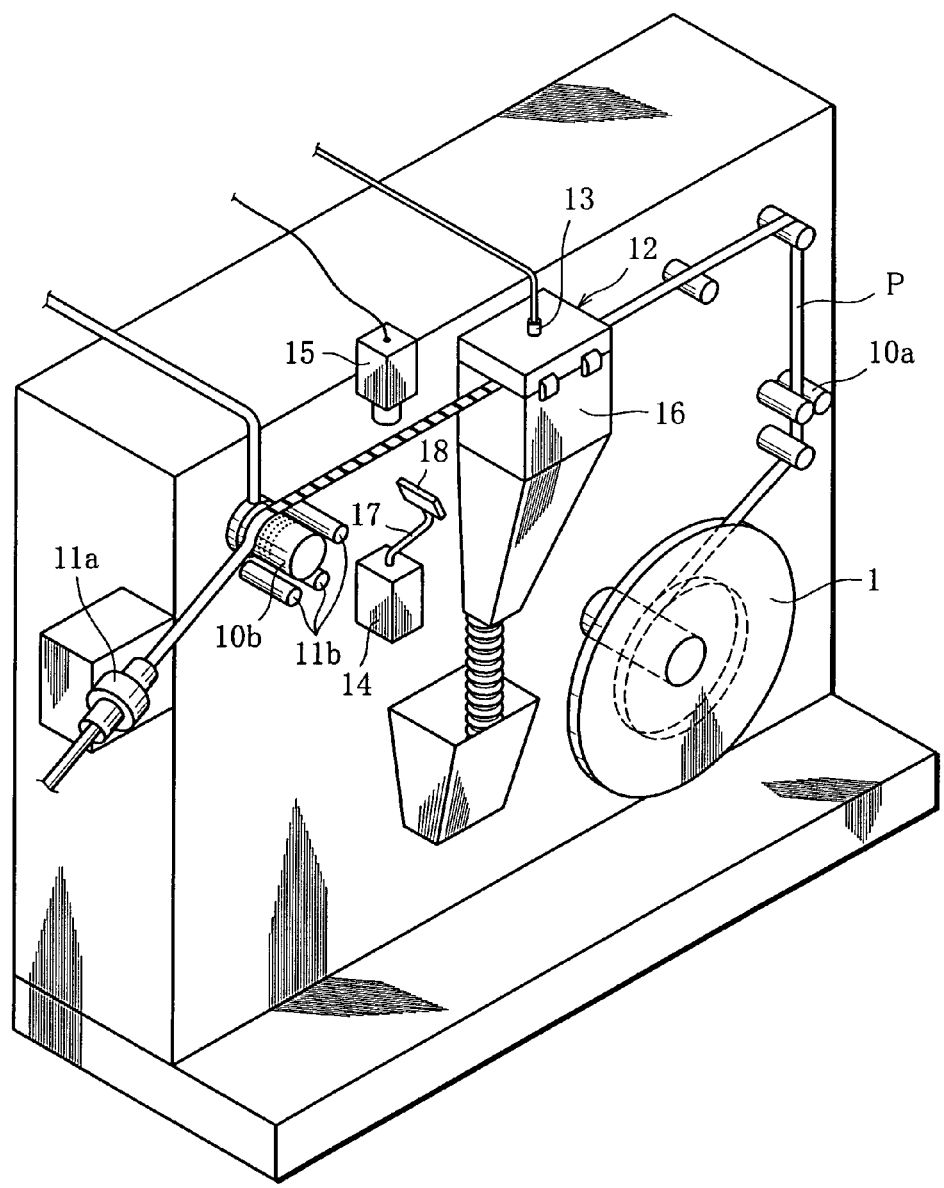
FIG. 1 is a diagram showing a schematic whole structure of a wrapping paper inspection apparatus according to this invention.

Referring to the drawings, a wrapping paper inspection apparatus according to the invention will be described.

Figure 2:
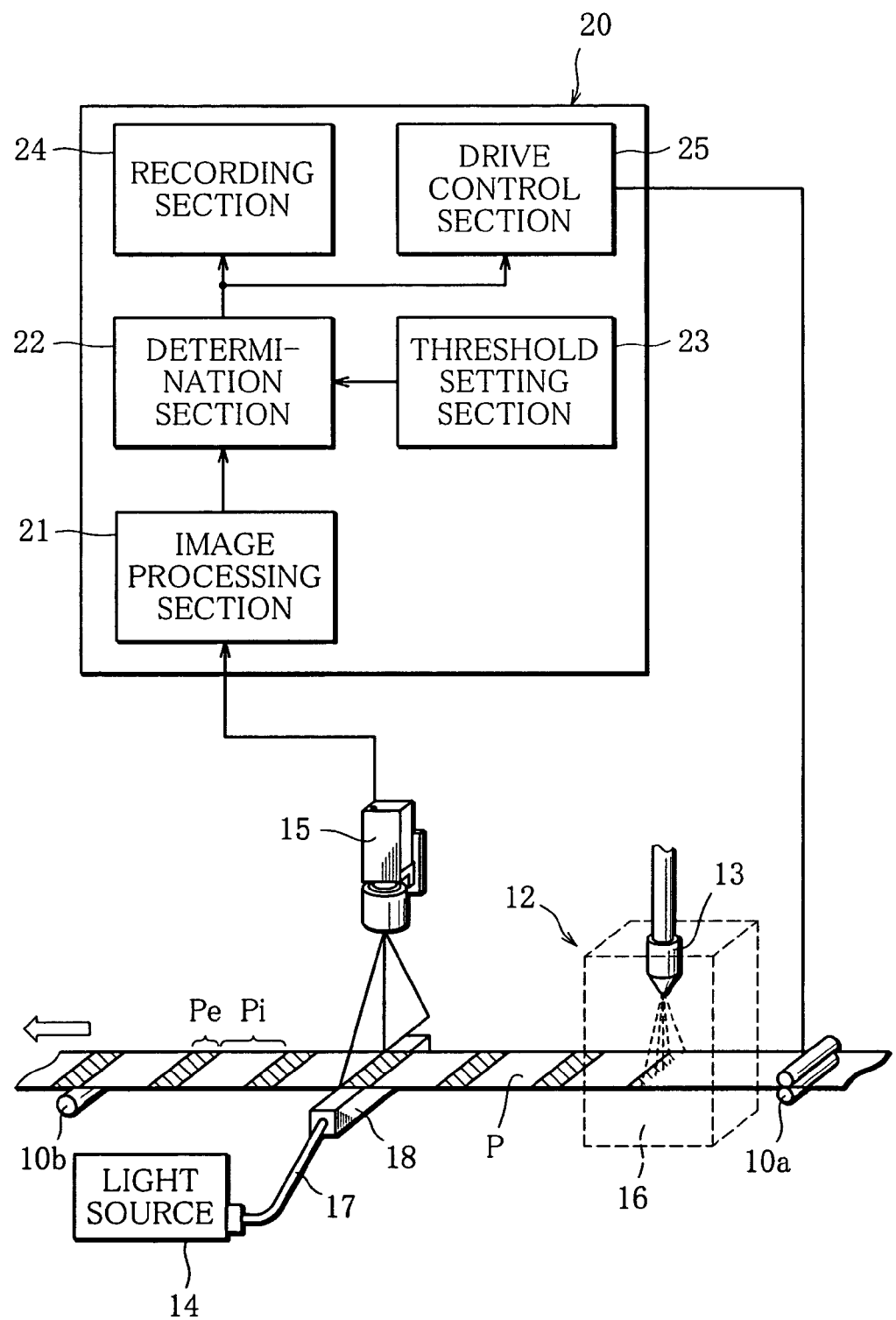
FIG. 2 is a diagram showing a schematic structure of an image pickup section and a wrapping paper inspection section of a wrapping paper inspection apparatus according to this invention.

In FIGS. 1 and 2, a wrapping paper inspection apparatus has a reel 1 on which wrapping paper P is wound and a pair of feed rollers 10a between which the wrapping paper P is held so that the wrapping paper P is unwound off the reel 1 as the feed rollers 10a rotate. The wrapping paper P unwound is discharged after passing through an inspection liquid application section 12, a suction roller 10b, and a jet air section 11a.

The suction roller 10b is formed at its circumferential face with a large number of air suction openings, and stretches the wrapping paper P horizontally between itself and the feed rollers 10a by sucking the wrapping paper P by means of a suction pump not shown. The jet air section 11a is cylindrical in shape and can create therein a flow of air flowing in one direction by means of an air supply unit not shown.

By this jet air section 11a, the wrapping paper P sucked and stuck around the suction roller 10b is separated off the suction roller 10b and discharged.

In the wrapping paper inspection apparatus arranged as described above, features characteristic of the present invention are: one side of the wrapping paper is wetted by spraying a liquid infiltrative to the wrapping paper (water or a volatile liquid, for example) onto the one side (low flame spread material portions) of the wrapping paper P applied with a diluted solution of a low flame spread material such as sodium alginate, the liquid being sprayed through a nozzle 13 provided in the inspection liquid application section 12; light is irradiated from a light source 14 onto the wrapping paper P wetted with the liquid; and an image pickup section (line sensor camera) 13 is provided to pick up light transmitted through the wrapping paper P.

The wrapping paper P coated in stripes with a diluted solution of sodium alginate, which is a low flame spread material, has the following characteristic: When a liquid infiltrative to the wrapping paper P, such as water, is sprayed through the nozzle 13 onto the coated side of the wrapping paper, the speed at which the liquid infiltrates into those regions (band portions) Pe of the wrapping paper which are applied with the diluted solution of sodium alginate, namely low flame spread material portions, is lower than the speed of infiltration of the liquid into those regions (band portions) Pi of the wrapping paper to which the solution is not applied. Thus, in the regions (band portions) Pe applied with the solution, the light transmittance decreases and the reflectance increases. As for wrapping paper to which a low flame spread property is imparted by increasing its thickness by affixing paper or layer (hereinafter simply referred to as low flame spread material) containing a low flame spread material, there is also such a characteristic that, due to a difference in the infiltration speed of the liquid, the light transmittance or reflectance of the wrapping paper P differs between the regions (band portions) Pe in which the low flame spread material is affixed to the base cigarette paper and the regions (base portions) Pi in which it is not affixed.

Paying attention to these points, the present invention is characterized in that the quality of application of the low flame spread material is optically inspected, utilizing a difference in light transmittance or reflectance between the regions (band portions) Pe applied with the low flame spread material and the regions (base portions) Pi not applied with such material, the difference being produced when the infiltrative liquid is sprayed to the side of the wrapping paper P applied with a diluted solution of sodium alginate.

This invention is alternatively characterized in that the quality of affixation of the low flame spread material is optically inspected, utilizing a difference in light transmittance or reflectance between the regions (band portions) Pe affixed with the low flame spread material and the regions (base portions) Pi not affixed with such material, the difference being produced when the wrapping paper P to which the low flame spread material is affixed at approximately equal intervals is wetted with the infiltrative liquid, as mentioned above.

Referring to FIG. 2, how wrapping paper P applied with sodium alginate, which is a low flame spread material, in approximately equally spaced stripes is inspected by the wrapping paper inspection apparatus arranged as described above will be described more in detail.

Wrapping paper P unwound from a roll 1 by means of feed rollers 10a is stretched horizontally by means of a suction roller 10b. Above the wrapping paper P stretched horizontally, there is provided a nozzle 13 for spraying an infiltrative liquid onto the side of the wrapping paper P applied with a diluted solution of sodium alginate. The nozzle 13 is provided with a cover 16 surrounding the nozzle, whereby the inspection liquid application section 12 is formed. The cover 16 of the inspection liquid application section 12 serves to prevent the liquid sprayed through the nozzle 13 onto the wrapping paper P from being scattered to the surroundings.

The nozzle 13 is adapted to spay an infiltrative liquid, such as water, onto the wrapping paper P to wet it. Onto the wrapping paper P wetted by means of the nozzle 13, light is projected from a light source 14 arranged under it. Specifically, light emitted from the light source 14 is transmitted through an optical fiber 17 to reach a light guide 18 formed with a slit, and is then projected from the light guide 18 in a direction (widthwise direction) perpendicular to the direction of travel of the wrapping paper P.

An optical sensor (line sensor camera, for example) 15 is provided so as to face the light guide 18, with the wrapping paper P interposed therebetween. The optical sensor (line sensor camera) 15 measures the amount of light projected from the light guide 18 to the wrapping paper P and transmitted through the wrapping paper P. The optical sensor (line sensor camera) 15 has a field of view that is a narrow linear region extending perpendicular to the direction of travel of the wrapping paper P. An image signal about the transmitted light photographed by the optical sensor (line sensor camera) 15 is supplied to a wrapping paper inspection section 20 for inspecting the quality of application of the low flame spread material to the wrapping paper P.

The wrapping paper inspection section 20 includes an image processing section 21 for converting image data obtained by the optical sensor (line sensor camera) 15 into luminance values. As described later in detail, the wrapping paper inspection section 20 includes a determination section 22 which discriminates between a region (band portion) Pe of the wrapping paper P coated with the low flame spread material and an uncoated region (base portion) Pi thereof by comparing a luminance value obtained by conversion in the image processing section 21 with a predetermined luminance value preset in a threshold setting section 23.

Figure 3:
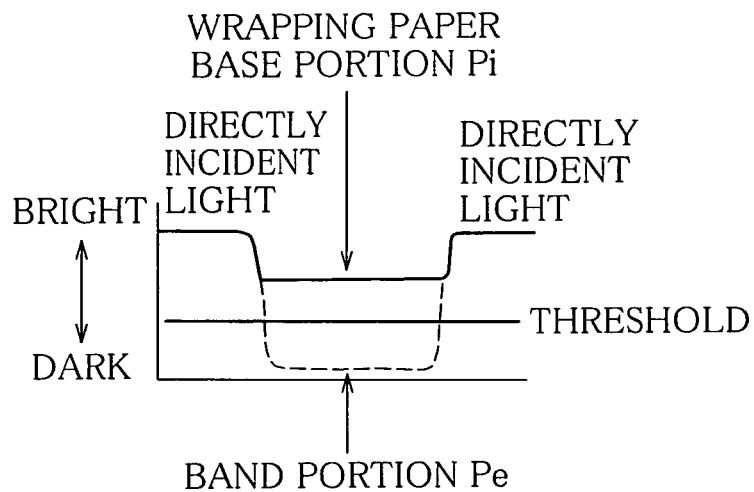
FIG. 3 is a diagram showing a difference in luminance between a wrapping-paper portion and a band portion coated with a low flame spread material, the difference being determined based on a luminance signal converted from an image signal in the wrapping paper inspection apparatus according to this invention.
Figure 4:
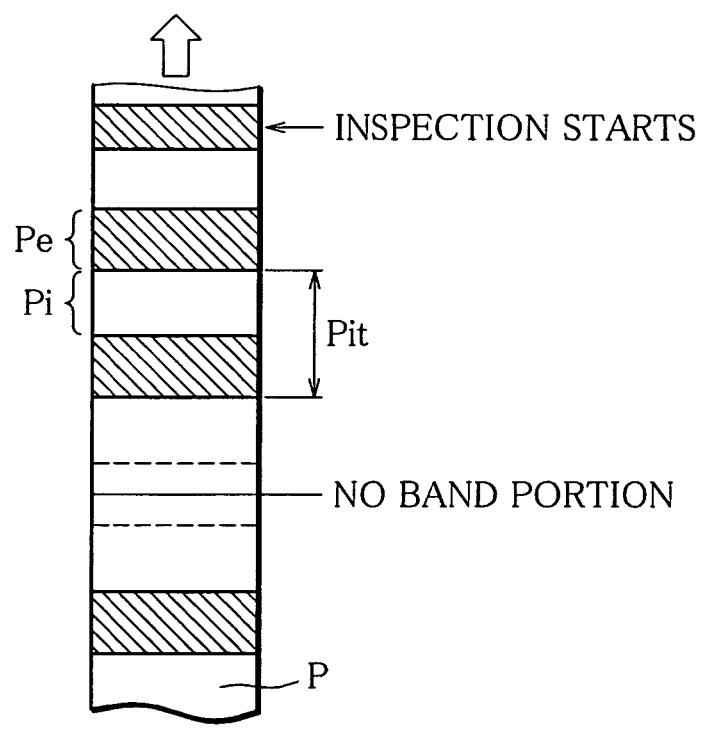
FIG. 4 is a diagram showing wrapping paper applied with a low flame spread material in stripes.

In accordance with luminance value level, luminance values obtained by conversion in the image processing section 21 are graded on a scale of 256 grades from 0 to 255, for example. As already mentioned, there is a difference in light transmittance between the base portions Pi and the band portions Pe, and hence the luminance value level of a band portion Pe is lower than that of a base portion Pi as shown in FIG. 3. The luminance value obtained when light from the light guide 18 is directly incident on the line sensor camera 15 is 255, and the luminance value obtained when light is not incident on the line sensor camera 15 is 0.

When the wrapping paper P is wetted by spraying infiltrative water or a liquid onto the side thereof applied with a low flame spread material, the infiltration speed of the applied liquid is low in the band portions Pe of the wrapping paper P, whereby the light transmittance of the wrapping paper P decreases and the luminance value decreases. In the regions (base portions) Pi not coated with the low flame spread material, the liquid applied infiltrates at a high speed, so that the light transmittance is high and the luminance value is large. When the threshold setting section 23 is set, as a threshold, with a luminance value approximately intermediate between the luminance value of the regions (band portions) Pe of the wrapping paper P coated with the low flame spread material and the luminance value of the uncoated regions (base portions) Pi thereof, the determination section 22 can identify the regions (band portions) Pe coated with the low flame spread material and the uncoated regions (base portions) Pi. A result of determination by the determination section 22 is recorded in a recording section 24.

Around the suction roller 10b, an air blower 11b is provided to blow off the liquid sprayed on the wrapping paper P. The air blower 11b prevents the liquid that wets the wrapping paper P from remaining on the suction roller 10b and causing the wrapping paper P to adhere around the suction roller 11b. Alternatively, it can be arranged to dry the liquid on the suction roller 10b using for example a heater instead of the air blower 11b.

Next, how wrapping paper is inspected by the wrapping paper inspection apparatus arranged as described above will be described.

First, wrapping paper P is unwound from a roll 1 and set to extend through between the feed rollers 10a, and through the inspection liquid application section 12, the suction roller 10b and the jet air section 11a. Then, an infiltrative liquid (water, for example) is sprayed through the nozzle 13 onto the side of the wrapping paper P applied with a diluted solution of sodium alginate. As mentioned above, the infiltration speed of the liquid differs between the regions (band portions) Pe of the wrapping paper P coated with the diluted solution of sodium alginate, which is a low flame spread material, and the uncoated regions (base portions) Pi thereof. When the infiltrative liquid is sprayed through the nozzle 13, the light transmittance becomes lower in the regions (band portions) Pe in which the diluted solution of sodium alginate is applied than in the regions (base portions) Pi in which it is not applied. This makes the stripe pattern identifiable. The band portions Pe are positioned within the field of view of the line sensor camera 15.

When the wrapping paper inspection apparatus is put into operation, the wrapping paper P wound into the roll 1 is continuously moved and discharged by means of the feed rollers 10a and the suction roller 10b, an infiltrative liquid (water, for example) is sprayed through the nozzle 13 onto the side of the wrapping paper P on which a diluted solution of sodium alginate is applied. As mentioned above, when the liquid is sprayed on the wrapping paper P, the light transmittance decreases in the regions (band portions) Pe applied with the diluted solution of sodium alginate, which is a low flame spread material, whereby the stripe pattern is made identifiable. The regions (band portions) Pe of the wrapping paper P coated with sodium alginate and the uncoated regions (base portions) Pi thereof pass through the field of view of the line sensor camera 15 alternately.

The line sensor camera 15 creates an image signal based on an picked-up image with the resolution of 15 lines per 1 mm, for instance, as viewed in a direction (the widthwise direction of the wrapping paper) perpendicular to the direction of travel of the wrapping paper P. The travel distance (feed length) of the wrapping paper is calculated from a rotation signal about the feed rollers 10a. Based on variation in luminance value of the image signal while the wrapping paper is travelling, the width of each of the regions (band portions) Pe coated with the diluted solution of sodium alginate and the distance (pitch) Pit between the coated regions are measured. Results of the measurement are stored in the recording section 24.

The next coated region (band portion) Pe is determined based on the measured distance (pitch) between the coated regions. If a decrease in luminance value (dark region), namely a band portion Pe, is not detected after the wrapping paper travels, for example 20 mm+several mm or more from the last coated region, it is determined that there is no band portion Pe coated with the low flame spread material there, and this information is stored in the recording section 24. If lack of a band portion Pe is detected, for example n times in succession, an abnormal signal is output so that the wrapping paper inspection apparatus will be stopped, for example.

When the whole wrapping paper P has been fed from the roll 1 and the inspection of the wrapping paper P has been finished, light emitted from the light guide 18 arrives at the line sensor camera 15 without being obstructed by the wrapping paper P. In that case, the luminance value obtained by the image processing section 21 becomes equal to the maximum value (255, for example). When the maximum value is detected, a drive control section 25 stops driving the feed rollers 10a, whereby a series of inspections is completed.

The embodiment described above uses a difference between the infiltration speed of an infiltrative liquid applied to the wrapping paper P into the regions (band portions) Pe coated with the low flame spread material and the infiltration speed of the liquid into the uncoated regions (base portions) Pi. In other words, the embodiment is based on an inspection technique using the fact that the difference in infiltration speed produces a difference in the amount of light transmitted through the wrapping paper P. In the detection of defects in the regions of the wrapping paper P coated with the low flame spread material, the amount of light (luminance) reflected from the wrapping paper P may be detected by means of a line sensor camera 15, instead of detecting the amount of light transmitted through the wrapping paper P. Although not depicted, in this case, a line sensor camera 15 and a light guide 18 of the wrapping paper inspection apparatus are arranged on the side of the wrapping paper P applied with a diluted solution of sodium alginate, and are positioned so that light projected from the light guide 18 to the wrapping paper P and reflected therefrom arrives at the line sensor camera 15. In the other respects, this wrapping paper inspection apparatus is similar in structure to the above-described wrapping paper inspection apparatus using transmitted light, and hence the detailed description thereof will be omitted.

As mentioned above, when water or a volatile liquid infiltrative to the wrapping paper is sprayed through the nozzle 13 onto the side of the wrapping paper applied with a diluted solution of sodium alginate, which is a low flame spread material, the infiltration speed differs between the regions (band portions) Pe coated with the low flame spread material and the uncoated regions (base portions) Pi, whereby a difference in light reflectance of the wrapping paper P is caused and the stripe pattern is made identifiable. In other words, the stripe pattern is detected by means of the line sensor 15 as variation in the amount of reflection of light projected from the light guide 18. By supplying the image data obtained by the line sensor camera 15 to the wrapping paper detection device 20, defects in the coating of the low flame spread material on the wrapping paper P can be detected as described above.

The wrapping paper inspection apparatus arranged as described above detects the quality of the coating of the low flame spread material by means of the line sensor camera 15, based on the fact that a difference in light transmittance or light reflectance is produced between the region (band portions) Pe coated with the low flame spread material and the uncoated regions (base portions) Pi when the side of the wrapping paper P applied with a diluted solution of sodium alginate is wetted with an infiltrative liquid. Thus, the quality of the low flame spread material coated on the wrapping paper can be inspected reliably.

Although the embodiment described above is a wrapping paper inspection apparatus arranged to inspect wrapping paper P applied with a diluted solution of sodium alginate serving as a low flame spread material, such inspection can be made also on wrapping paper P to which pieces of paper (hereinafter referred to as low flame spread material) which is similar in material to base cigarette paper and contains a low flame spread material are affixed in equally spaced stripes, for example, so that the wrapping paper is imparted with a low flame spread property resulting from the thickness difference in the wrapping paper and the low flame spread material contained therein.

As mentioned above, this inspection uses the fact that the infiltration speed of a liquid differs between the regions (base portions) Pi of the wrapping paper P to which the low flame spread material is not affixed and the regions (band portions) Pe thereof affixed with the low flame spread material. In other words, the inspection utilizes the fact that, due to the aforementioned difference in infiltration speed, a difference is caused in the amount of light transmitted through the wrapping paper P (light transmittance) and the amount of light reflected from the wrapping paper (light reflectance) when the wrapping paper P is wetted with an infiltrative liquid sprayed thereonto.

More specifically, when the side of the wrapping paper P affixed with the low flame spread material is wetted with infiltrative water or a volatile liquid sprayed thereonto through the nozzle 13, the infiltration rate is higher in the regions (base portions) Pi not affixed with the low flame spread material than in the regions (band portions) Pe affixed with the low flame spread material. Hence, in the former regions, the light transmittance increases and the light reflectance decreases, which makes the stripe pattern identifiable. The stripe pattern is detected by means of the line sensor camera 15 as variation in the amount of light projected from the light guide 18 and transmitted through or reflected from the wrapping paper.

Thus, defects in low flame spread material portions of the wrapping paper P (defects in the coating or affixation of the low flame spread material to the wrapping paper) can be positively detected by the wrapping paper inspection apparatus arranged as described above, in which the quality of the coating or affixation of the low flame spread material is detected by means of the line sensor camera 15, using the fact that when the wrapping paper P coated or affixed with the low flame spread material is wetted with an infiltrative liquid, a difference in light transmittance or light reflectance is produced between the regions (band portions, or low flame spread material portions) Pe coated or affixed with the low flame spread material and the uncoated or unaffixed regions (base portions) Pi.

Figure 5:
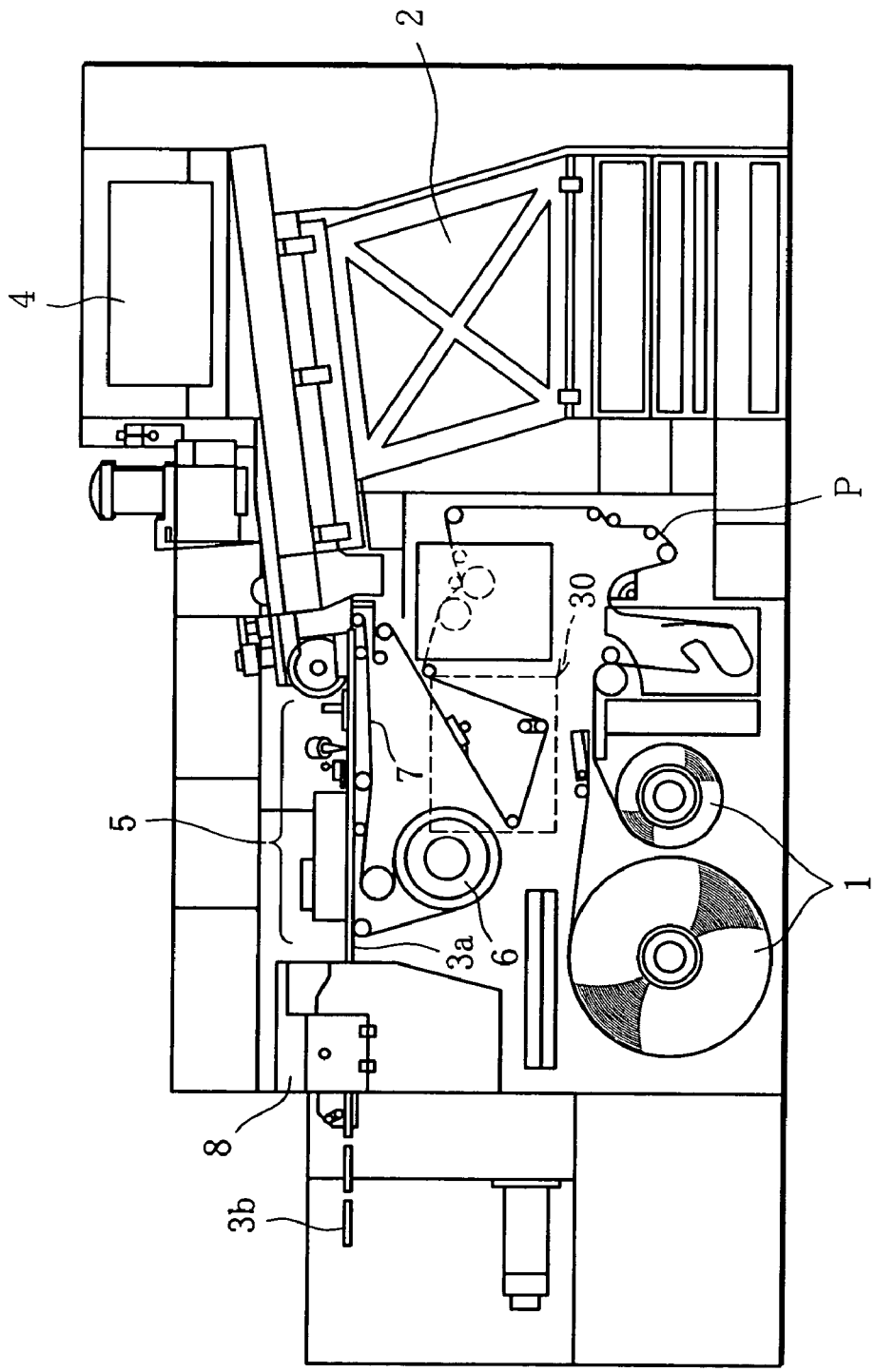
FIG. 5 is a diagram showing a schematic structure of a tobacco wrapping machine using a wrapping paper inspection apparatus according to this invention.

Next, referring to the drawings, a tobacco wrapping machine using a wrapping paper inspection apparatus according to this invention will be described. As shown in FIG. 5, the tobacco wrapping machine is designed to suck tobacco shreds 3, which are supplied into a hopper 2, onto a transport belt (tobacco band) 3a in a suction section 4, transport it to a paper wrapping section 5, and roll up the tobacco shreds 3 continuously with an elongated wrapping paper P which is continuously supplied from a roll.

The wrapping paper P is paper applied with a diluted solution of a low flame spread material, for example sodium alginate, in approximately equally spaced stripes, or paper having a low flame spread property imparted by a thickness difference in the wrapping paper P. The thickness difference is provided by, for example, affixing pieces of paper, similar in material to base cigarette paper and containing a low flame spread material, onto the wrapping paper P in approximately equally spaced stripes.

The paper wrapping section 5 is designed to continuously roll up the tobacco shreds 3 with the wrapping paper P to form a single elongated tobacco rod 3a, on a garniture tape 7 that is speed-controlled and driven to move basically by means of a main spindle 6. The tobacco rod 3a formed in the paper wrapping section 5 is cut to a predetermined length in a cutting section 8a arranged to the output side of the paper wrapping section. The resulting products 3b, which are for example approximately twice the length of a final cigarette and called double-length cigarettes, are successively supplied to a filter attachment apparatus, not shown, in the next process.

In the tobacco wrapping machine described above, a distinctive feature of the present invention is that a wrapping paper inspection apparatus 30 is arranged in a transport path in which the wrapping paper P is unwound and continuously fed to the paper wrapping section 5, to continuously inspect the wrapping paper P to make cigarettes with the wrapping paper P inspected.

Figure 6:
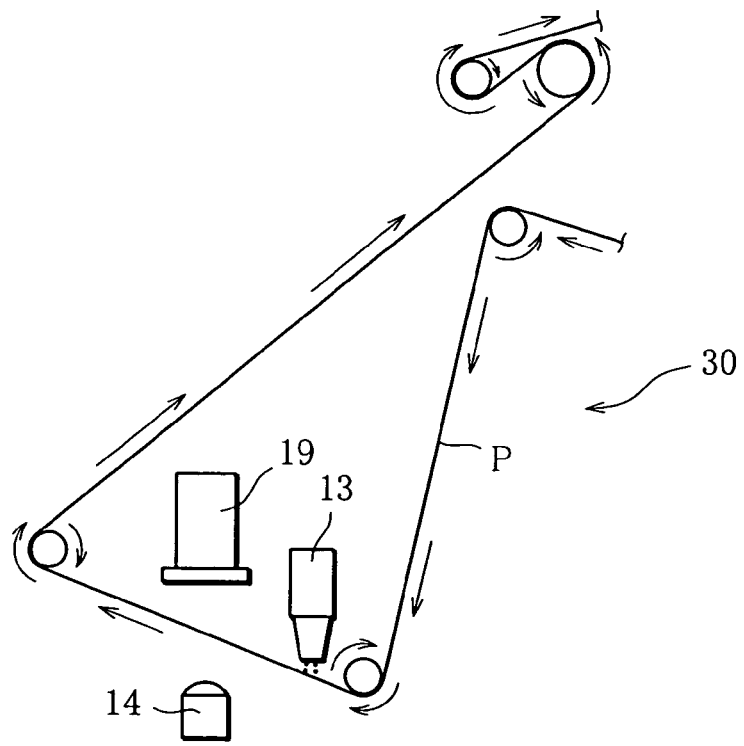
FIG. 6 is a diagram showing a structure of essential parts of a wrapping paper inspection apparatus incorporated in a tobacco wrapping machine according to this invention.

In other words, this tobacco wrapping machine can make cigarettes continuously at a high speed, while inspecting whether or not there are defects in those portions of the wrapping paper P coated or affixed with a low flame spread material. Referring to FIG. 6 showing a structure of essential parts, a wrapping paper inspection apparatus 30 of a tobacco wrapping machine according to this distinctive invention will be further described.

The wrapping paper inspection apparatus 30 is arranged in a transport path for wrapping paper P coated or affixed with a low flame spread material, and includes a nozzle 13 for applying an infiltrative liquid (water or a volatile liquid, for example) in a straight line onto the side of the wrapping paper P coated or affixed with the low flame spread material. An optical sensor 19 is arranged on the side of the wrapping paper P on which water or a volatile liquid is applied in a straight line by means of the nozzle 13.

A light source 14 is arranged to face the optical sensor 19 with the wrapping paper P interposed therebetween, so that light projected from the light source 14 is transmitted through the wrapping paper P and arrives at the optical sensor 19. In other words, the light source 14 and the optical sensor 19 are so combined as to detect light transmitted through the wrapping paper P.

Figure 7:
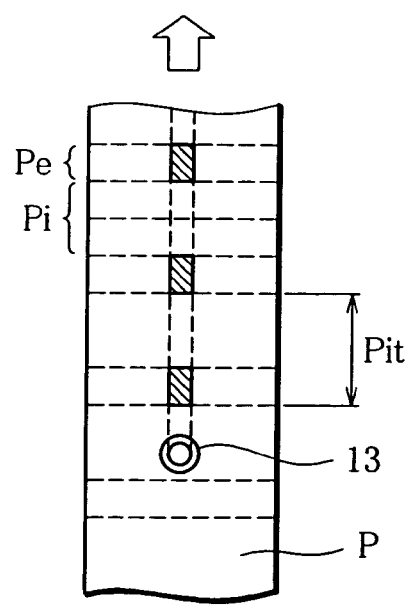
FIG. 7 is a diagram showing wrapping paper applied with a low flame spread material in stripes.

In particular, when an infiltrative liquid is applied in a straight line on the side of the wrapping paper P coated with the low flame spread material, the infiltration speed of the infiltrative liquid (water, for example) differs between regions (band portions) Pe coated with the low flame spread material and the uncoated regions (base portions) Pi, as shown in FIG. 7. In other words, when an infiltrative liquid is applied by means of the nozzle 13, the infiltration speed of water differs between the regions (band portions) Pe coated with a diluted solution of sodium alginate and uncoated regions (base portions) Pi. This produces a difference in light transmittance or reflectance of the wrapping paper P, and a difference is caused in the amount of light transmitted through or reflected from the wrapping paper P. An image signal about the transmitted or reflected light detected by the optical sensor 19 is supplied to a wrapping paper inspection section 20 for inspecting the quality of the low flame spread material coated on the wrapping paper P.

Also in the case of wrapping paper affixed with the low flame spread material, the infiltration speed of the liquid and by extension the light transmittance or reflectance differs between regions affixed with the low flame spread material and unaffixed regions. Based on an image signal about the transmitted or reflected light detected by the optical sensor 19, the wrapping paper inspection section 20 can inspect the quality of affixation of the low flame spread material to the wrapping paper.

The functional specifics of the wrapping paper inspection section 20 are similar to those of the wrapping paper inspection apparatus described before, and hence the detailed description thereof will be omitted. In brief, an image processing section 21 converts the image data obtained by the optical sensor 19 into luminance values, and a determination section 22 identifies the regions (band portions) Pe of the wrapping paper P coated or affixed with the low flame spread material and the uncoated or unaffixed regions (base portions) Pi thereof, by comparing the luminance values with a luminance value preset in a threshold setting section 23. Results of determination by the determination section 22 are recorded in a recording section 24.

Although illustration is omitted, in a case where the wrapping paper P is inspected using light reflected from the wrapping paper P, both the optical sensor 19 and the light source 14 are disposed on that side of the wrapping paper P to which the low flame spread material is applied or affixed so that light projected from the light source 14 to the wrapping paper P is reflected from the wrapping paper P and arrives at the optical sensor 19. Defects in the low flame spread material applied or affixed to the wrapping paper P can be detected by supplying the image data obtained by the optical sensor 19 to the wrapping paper inspection section 20.

As understood from the above, in the tobacco wrapping machine according to the invention, since the infiltrative liquid (water or a volatile liquid, for example) is applied in a straight line onto the side of the wrapping paper P applied or affixed with the low flame spread material by means of the nozzle 13, the liquid can quickly diffuse in the wrapping paper P after the inspection of the wrapping paper P. This makes it possible to detect defects in the low flame spread material portions of the wrapping paper P at a high speed, without obstructing cigarette making.

When the wrapping paper P is inspected using light transmitted through the wrapping paper P, the installation positions of the optical sensor 19 and the light source 14 can be reversed. What is essential is to arrange the optical sensor 19 and the light source 14 to face each other with the wrapping paper P interposed therebetween.

In other respects, the present invention can be modified in various ways without deviating from its scope.

The invention claimed is:

1. A wrapping paper inspection apparatus for inspecting wrapping paper with a low flame spread material arranged in stripes on one side thereof, comprising:
    a liquid application section including a nozzle arranged in a wrapping-paper discharge path, in which the wrapping paper is unwound and continuously discharged, for spraying a volatile liquid onto the one side of the wrapping paper and wetting the one side of the wrapping paper with said volatile liquid, the volatile liquid showing a difference in infiltration rate between base portions of the wrapping paper not affixed with the low flame spread material and the stripes of low flame spread material;

an image pickup section including an image pickup position defined on the wrapping-paper discharge path downstream of said nozzle, for irradiating light to the wrapping paper wetted with the volatile liquid by said nozzle at the image pickup position while the volatile liquid is being infiltrated into the wrapping paper, detecting the light transmitted through the wrapping paper or the light reflected from the one side of the wrapping paper, and generating an image signal on the basis of the detected light; and a wrapping paper inspection section for determining defects in the low flame spread material on the wrapping paper from the image signal generated by said image pickup section; and an air blower configured to blow off liquid sprayed on the wrapping paper, the air blower being arranged downstream from image pickup section.

2. The wrapping paper inspection apparatus according to claim 1, wherein the wrapping paper inspection section includes:

an image processing section for converting the image signal generated by said image pickup section into a luminance signal, a determination section for determining defects in the low flame spread material on the wrapping paper by comparing the luminance signal obtained by conversion in said image processing section with a predetermined luminance value, and a recording section for recording the defects in the low flame spread material on the wrapping paper determined by said determination section.

3. The wrapping paper inspection apparatus according to claim 1, wherein the volatile liquid is water.

4. The wrapping paper inspection apparatus according to claim 1, further comprising at least one feed roller arranged upstream of the nozzle and a suction roller arranged downstream of the image pickup section, the wrapping paper extending between the at least one feed roller and the suction roller.

5. The wrapping paper inspection apparatus according to claim 1, wherein the image pickup section includes:

a light source connected to a light guide, the light guide being arranged below the wrapping paper; and an optical sensor located opposite the light source above the wrapping paper to detect light transmitted through the wrapping paper.

6. The wrapping paper inspection apparatus according to claim 5, wherein the light source and the optical sensor are arranged perpendicular to the wrapping paper discharge path.

7. A tobacco wrapping machine for continuously wrapping tobacco shreds with wrapping paper with a low flame spread material arranged in stripes on one side thereof to form a tobacco rod, then cutting the tobacco rod to a predetermined length, and successively supplying tobacco rods of the predetermined length to a next process, comprising:

a liquid application section including a nozzle arranged in a wrapping-paper feeding path, in which the wrapping paper is unwound and continuously fed, for spraying a volatile liquid into the one side of the wrapping paper and wetting the one side of the wrapping paper with the volatile liquid, the volatile liquid showing a difference in infiltration rate between base portions of the wrapping paper not affixed with the low flame spread material and the stripes of low flame spread material;

an image pickup section including an image pickup position defined on the wrapping-paper feeding path downstream of said nozzle, for irradiating light to the wrapping paper wetted with the volatile liquid by said nozzle at the image pickup position while the volatile liquid is being infiltrated into the wrapping paper, picking up the light transmitted through the wrapping paper or the light reflected from the one side of the wrapping paper, and generating an image signal on the basis of the detected light; and a wrapping paper inspection section for determining whether there are defects in the low flame spread material on the wrapping paper from the image signal generated by said image pickup section, and recording a result of determination; and an air blower configured to blow off liquid sprayed on the wrapping paper, the air blower being arranged downstream from image pickup section.

8. The tobacco wrapping machine according to claim 7, wherein the volatile liquid is water.

9. The tobacco wrapping machine apparatus according to claim 7, further comprising at least one feed roller arranged upstream of the nozzle and a suction roller arranged downstream of the image pickup section, the wrapping paper extending between the at least one feed roller and the suction roller.

10. The tobacco wrapping machine apparatus according to claim 7, wherein the image pickup section includes:

a light source connected to a light guide, the light guide being arranged below the wrapping paper; and an optical sensor located opposite the light source above the wrapping paper to detect light transmitted through the wrapping paper.

11. The tobacco wrapping machine apparatus according to claim 10, wherein the light source and the optical sensor are arranged perpendicular to the wrapping paper discharge path.

* * * * *